US005547968A

United States Patent [19]
Ueno

[11] Patent Number: 5,547,968
[45] Date of Patent: Aug. 20, 1996

[54] TREATMENT OF OCULAR HYPERTENSION WITH A SYNERGISTIC COMBINATION

[75] Inventor: Ryuji Ueno, Hyogo-ken, Japan

[73] Assignee: R-Tech Ueno, Ltd., Osaka, Japan

[21] Appl. No.: 487,637

[22] Filed: Jun. 7, 1995

Related U.S. Application Data

[63] Continuation of Ser. No. 352,822, Dec. 1, 1994, abandoned, which is a continuation of Ser. No. 51,434, Apr. 23, 1993, abandoned, which is a continuation of Ser. No. 833,025, Feb. 10, 1992, abandoned.

[30] Foreign Application Priority Data

Mar. 1, 1991 [JP] Japan .................... 3-061328

[51] Int. Cl.$^6$ .................... A61K 31/41; A61K 31/215; A61K 31/19
[52] U.S. Cl. .................... 514/363; 514/530; 514/573; 514/913
[58] Field of Search .................... 514/363, 530, 514/573, 913

[56] References Cited

U.S. PATENT DOCUMENTS 5,001,153  3/1991  Ueno et al. .................... 514/530

FOREIGN PATENT DOCUMENTS 0366279  9/0989  European Pat. Off. .
0308135  9/1988  European Pat. Off. .

OTHER PUBLICATIONS

Embase, embase No. 89199131; M. F. Sugrue: "The pharmacology of antiglaucoma drugs", & Pharmacol. Ther., 1989, 43/1 (91–138).

Embase, embase no. 82085670; M. Beausang–Linder: "Effects of sympathetic stimulation on cerebral and ocular blood flow. Modification by hypertension, hypercapnia, acetazolamide, PGIsub 2 and papaverine", & Acta Physiol. Scand., 1982, 114/2 (217–224).

J. Pharmacol. Exp. Ther. (USA), 1985, 232/2 (534–540) Sugrue et al. (See the Embase abstract).

*Primary Examiner*—Zohreh Fay
*Attorney, Agent, or Firm*—Sughrue, Mion, Zinn, Macpeak & Seas

[57] ABSTRACT

A method for treatment of ocular hypertension which comprises ocularly administering, to a subject in need of such treatment, an oculo-hypotensively synergistic combination of (a) a 15-ketoprostaglandin or a pharmaceutically acceptable salt thereof, or a pharmaceutically acceptable ester thereof, and
(b) a carbonate dehydratase inhibitor in an amount effective in treatment of ocular hypertension.

9 Claims, No Drawings

TREATMENT OF OCULAR HYPERTENSION WITH A SYNERGISTIC COMBINATION

This is a Continuation of application Ser. No. 08/352,822 filed Dec. 1, 1994 now abandoned, in turn a continuation of application Ser. No. 08/051,434, Apr. 23, 1993, abandoned, in turn a continuation of application Ser. No. 07/833,025, Feb. 10, 1992, abandoned.

BACKGROUND OF THE INVENTION

1. Field of the Invention

The present invention relates to a treatment of ocular hypertension with a synergistic combination comprising (a) a 15-ketoprostaglandin compound and (b) a carbonate dehydratase inhibitor. Said combination is characterized by an improved effect and a reduced side-effect.

The compounds used as the component (a) in the present invention are prostaglandin analogues which can be obtained synthetically.

2. Information of Prior Art

Prostaglandins (hereinafter, prostaglandins are referred to as PGs) are members of a class of organic carboxylic acid that are contained in human and most other mammalian tissues or organs and that exhibit a wide range of physiological activities. Naturally occurring PGs possess as a common structural feature the prostanoic acid skeleton:

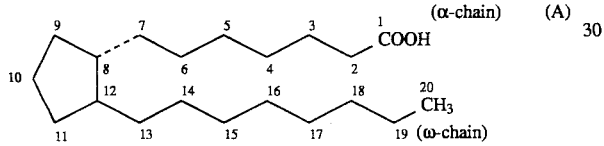

Some synthetic analogues have somewhat modified skeletons. The primary PGs are classified based on the structural feature of the five-membered cycle moiety into PGAs, PGBs, PGCs, PGDs, PGEs, PGFs, PGGs, PGHs, PGIs and PGJs, and also on the presence or absence of unsaturation and oxidation in the chain moiety as:

| | |
|---|---|
| Subscript 1 | 13,14-unsaturated-15-OH |
| Subscript 2 | 5,6- and 13,14-diunsaturated-15-OH |
| Subscript 3 | 5,6- 13,14- and 17,18-triunsaturated-15-OH |

Further, PGFs are sub-classified according to the configuration of hydroxy group at position 9 into α(hydroxy group being in the alpha configuration) and β(hydroxy group being in the beta configuration).

The fact that the above compounds under item (a) have ocular hypotensive activity has been known by Japanese Patent Publication No. A-108/1990 and No. A-96528/1990. The carbonate dehydratase inhibitor referred to under item (b) refers to the agents capable of specifically inhibiting enzymes which take part in the reversible reaction forming carbonate from carbon dioxide and water in living organisms, and is known to have pharmacological activities such as ocular hypotension. It has also been described in Japanese Patent Publication A-313728/1988 that prostaglandins can be coadministered with an adrenergic blocker. Such description, however, neither show a combined use of the carbonate dehydratase inhibitor and the component (a) in the present invention nor suggest that said combined use may cause synergistic increase in effect or decrease in side-effect because the adrenergic blockers are agents which inhibit the binding of the adrenergic agents with the adrenergic receptors thus exerting their pharmacological activity.

After an extensive study on the possibility that the effect of the component. (a) in the present invention is improved by combining it with a variety of compounds, the present inventor has surprisingly discovered that the effect of the component (a) is significantly improved and side-effect is decreased by co-administration with a carbonate dehydratase inhibitor such as acetazolamide. Said discovery leads to the present invention.

SUMMARY OF THE INVENTION

In a first aspect, the present invention provides a method for treatment of ocular hypertension which comprises ocularly administering, to a subject in need of such treatment, an oculo-hypotensively synergistic combination of (a) a 15-ketoprostaglandin or a pharmaceutically acceptable salt thereof, or a pharmaceutically acceptable ester thereof, and (b) a carbonate dehydratase inhibitor in an amount effective in treatment of ocular hypertension.

In a second aspect, the present invention provides a use of an oculo-hypotensively synergistic combination of (a) a 15-ketoprostaglandin or a pharmaceutically acceptable salt thereof, or a pharmaceutically acceptable ester thereof, and (b) a carbonate dehydratase inhibitor for the manufacture of a medicament useful in treatment of ocular hypertension.

In a third aspect, the present invention provides a pharmaceutical composition for treatment of ocular hypertension which comprising an oculo-hypotensively synergistic combination of (a) a 15-ketoprostaglandin or a pharmaceutically acceptable salt thereof, or a pharmaceutically acceptable ester thereof, and (b) a carbonate dehydratase inhibitor in association with a pharmaceutically acceptable carrier, diluent or excipient.

DETAILED DESCRIPTION OF THE INVENTION

The "15-ketoprostaglandins", used as the component (a) in the present invention and referred to as the component (a), include any prostaglandin derivatives which have a single bond, a double bond or a triple bond between positions 13 and 14 and an oxo group in place of the hydroxy group at position 15 of the prostanoic acid nucleus.

Nomenclature

Nomenclature of the component (a) herein uses the numbering system of prostanoic acid represented in formula (A) shown above.

While formula (A) shows a basic skeleton having twenty carbon atoms, the 15-keto-PG compounds used in the present invention are not limited to those having the same number of carbon atoms. The carbon atoms in Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When the number of carbon atoms is decreased in the α-chain, the number is deleted in order starting from position 2 and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20 and when the number of carbon atoms is increased in the ω-chain, compounds are named as substituted derivatives herring respective substituents at position 20. Stereochemistry of the compounds is the same as that of above formula (A) unless otherwise specified. Thus, 15-keto-PGs compound having 10 carbon atoms in the ω-chain is nominated as 15-keto- 20-ethyl-PGs.

The above formula expresses a specific configuration which is the most typical one, and in this specification compounds having such a configuration are expressed without any specific reference to it.

In general, PGDs, PGEs and PGFs have a hydroxy group on the carbon atom at position 9 and/or 11 but in the present specification the term "15-keto-PGs" includes PGs having a group other than a hydroxyl group at position 9 and/or 11. Such PGs are referred to as 9-dehydroxy-9-substituted-PGs or 11-dehydroxy-11- substituted-PGs.

As stated above, nomenclature of the component (a) is based upon the prostanoic acid. These compounds, however, can also be named according to the IUPAC naming system. For example, 13,14-dihydro-15-keto-16R,S-fluoro-PGE$_2$ is (Z)-7-{(1R,2R,3R)-3-hydroxy-2-[(4R,S)-fluoro-3-oxo-1-octyl]-5-oxocyclopentyl}-hept-5-enoic acid. 13,14-dihydro-15-keto-20-ethyl-PGE$_2$ is (Z)-7-{(1R,2R,3R)-3-hydroxy- 2-[3-oxo-1-decyl]-5-oxocyclopentyl}-hept-5-enoic acid. 13,14-dihydro-15-keto-20-ethyl-PGF$_{2\alpha}$ isopropyl ester is isopropyl (Z)-7-[(1R,2R,3R,5S)-3,5-dihydroxy-2-{3-oxo-1-decyl)-cyclopentyl] -hept-5-enoate. 13,14-dihydro-15-keto- 20-methyl-PGF$_{2\alpha}$ methyl ester is methyl (Z)-7-[(1R,2R,3R,5S)- 3,5-dihydroxy-2-{3-oxo-1-nonyl}-cyclopentyl]-hept-5-enonate.

Preferred Compounds

The component (a) used in the present invention may be any derivatives of PG insofar as they are saturated or unsaturated between positions 13 and 14 and have an oxo group at position 15 in place of the hydroxy group, and may have no double bond (PG subscript 1 compounds), a double bond between positions 5 and 6 (PG subscript 2 compounds), or two double bonds between positions 5 and 6 as well as positions 17 and 18 (PG subscript 3 compounds).

Typical examples of the compounds used in the present invention are 15-keto-PGA$_1$, 15-keto-PGA$_2$, 15-keto-PGA$_3$, 15-keto-PGB$_1$, 15-keto-PGB$_2$, 15-keto-PGB$_3$, 15-keto-PGC$_1$, 15-keto-PGC$_2$, 15-keto-PGC$_3$, 15-keto-PGD$_1$, 15-keto-PGD$_2$, 15-keto-PGD$_3$, 15-keto-PGE$_1$, 15-keto-PGE$_2$, 15-keto-PGE$_3$, 15-keto-PGF$_1$, 15-keto-PGF$_2$, 15-keto-PGF$_3$, 13,14-dihydro-15-keto-PGA$_1$, 13,14-dihydro-15-keto-PGA$_2$, 13,14-dihydro-15-keto-PGA$_3$, 13,14-dihydro-15-keto-PGB$_1$, 13,14-dihydro-15-keto-PGB$_2$, 13,14-dihydro-15-keto-PGB$_3$, 13,14-dihydro-15-keto-PGC$_1$, 13,14-dihydro-15-keto-PGC$_2$, 13,14-dihydro-15-keto-PGC$_3$, 13,14-dihydro-15-keto-PGD$_1$, 13,14-dihydro-15-keto-PGD$_2$, 13,14-dihydro-15-keto-PGD$_3$, 13,14-dihydro-15-keto-PGE$_1$, 13,14-dihydro-15-keto-PGE$_2$, 13,14-dihydro-15-keto-PGE$_3$, 13,14-dihydro-15-keto-PGF$_1$, 13,14-dihydro-15-keto-PGF$_2$, 13,14-dihydro-15-keto-PGF$_3$, wherein PG is as defined above as well as their substitution products or derivatives.

Examples of substitution products or derivatives include pharmaceutically or physiologically acceptable salts and esters at the carboxy group at the alpha chain, unsaturated derivatives having a double bond or a triple bond between positions 2 and 3 or positions 5 and 6, respectively, substituted derivatives having substituent(s) on carbon atom(s) at position 3, 5, 6, 16, 17, 19 and/or 20 and compounds having lower alkyl or a hydroxy (lower) alkyl group at position 9 and/or 11 in place of the hydroxy group, of the above PGs.

Examples of substituents present in preferred compounds are as follows: Substituents on the carbon atom at position 3, 17 and/or 19 include lower alkyl, for example, $C_{1-4}$ alkyl, especially methyl and ethyl. Substituents on the carbon atom at position 16 include lower alkyl e.g. methyl, ethyl etc., hydroxy and halogen atom e.g. chlorine, fluorine, aryloxy e.g. trifluoromethylphenoxy, etc. Substituents on the carbon atom at position 17 include halogen atom e.g. chlorine, fluorine etc. Substituents on the carbon atom at position 20 include saturated and unsaturated lower alkyl e.g. $C_{1-6}$ alkyl, lower alkoxy e.g. $C_{1-4}$ alkoxy and lower alkoxy (lower) alkyl e.g. $C_{1-4}$ alkoxy-$C_{1-4}$ alkyl. Substituents on the carbon atom at position 5 include halogen atom e.g. chlorine, fluorine etc. Substituents on the carbon atom at position 6 include oxo group forming carbonyl. Stereochemistry of PGs having hydroxy, lower alkyl or lower (hydroxy) alkyl substituent on the carbon atom at position 9 and/or 11 may be alpha, beta or mixtures thereof.

Especially preferred compounds are those having a lower alkyl e.g. methyl, ethyl, propyl, isopropyl, butyl, hexyl, preferably $C_{2-4}$ alkyl and most preferably ethyl at position 20.

A group of preferred compounds used in the present invention has the formula

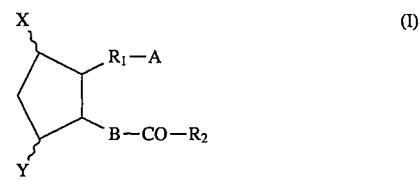

wherein X and Y are hydrogen, hydroxy, halo, lower alkyl, hydroxy(lower)alkyl, or oxo, with the proviso that at least one of X and Y is a group other than hydrogen, and 5-membered ring may have at least one double bond, A is —COOH or its pharmaceutically acceptable salt or ester, B is —CH$_2$—CH$_2$—, —CH=CH— or —C≡C—, R$_1$ is bivalent saturated or unsaturated, lower or medium aliphatic hydrocarbon residue which is unsubstituted or substituted with halo, oxo or aryl, R$_2$ is saturated or unsaturated, medium aliphatic hydrocarbon residue having 5 or more carbon atoms in the main or straight chain moiety which is unsubstituted or substituted with halo, hydroxy, oxo, lower alkoxy, lower alkanoyloxy, cyclo(lower)alkyl, aryl or aryloxy.

In the above formula, the term "unsaturated" in the definitions for R$_1$ and R$_2$ is intended to include at least one and optionally more than one double bond and/or triple bond isolatedly, separately or serially present between carbon atoms of the main and/or side chains. According to usual nomenclature, an unsaturation between two serial positions is represented by denoting the lower number of said two positions, and an unsaturation between two distal positions is represented by denoting both of the positions. Preferred unsaturation is a double bond at position 2 and a double or triple bond at position 5.

The term "lower or medium aliphatic hydrocarbon residue" or "medium aliphatic hydrocarbon residue" refers to a straight or branched chain hydrocarbyl group having 1 to 14 carbon atoms or 5 to 14 carbon atoms, respectively, (for a side chain, 1 to 3 carbon atoms being preferred) and preferably 2 to 8 carbon atoms for $R_1$ and 6 to 9 carbon atoms for $R_2$.

The term "halo" denotes fluoro, chloro, bromo and iodo.

The term "lower" throughout the specification is intended to include a group having 1 to 6 carbon atoms unless otherwise specified.

The term "lower alkyl" as a group or a moiety in hydroxy(lower)alkyl, monocyclic aryl(lower) alkyl, monocyclic aroyl(lower)alkyl or halo(lower)alkyl includes saturated and straight or branched chain hydrocarbon radicals containing 1 to 6, carbon atoms, e.g. methyl, ethyl, propyl, isopropyl, butyl, isobutyl, t-butyl, pentyl and hexyl.

The term "lower alkoxy" refers to the group lower-alkyl-O- wherein lower alkyl is as defined above.

The term "hydroxy(lower)alkyl" refers to lower alkyl as defined above which is substituted with at least one hydroxy group, e.g. hydroxymethyl, 1-hydroxyethyl, 2-hydroxyethyl and 1-methyl-1-hydroxyethyl.

The term "lower alkanoyloxy" refers to a group of the formula: RCO-O- wherein RCO- is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tolyl, xylyl and thienyl. Examples of substituents are halo and halo(lower)alkyl wherein halo and lower alkyl being as defined above.

The term "aryloxy" refers to a group of the formula: ArO- wherein Ar is aryl as defined above.

Suitable "pharmaceutically acceptable salts" includes conventional non-toxic salts, and may be a salt with an inorganic base, for example an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt, caffeine salt, etc.), a basic amino acid salt (e.g. arginine salt, lysine salt, etc.), tetraalkyl ammonium salt and the like. These salts can be prepared by the conventional process, for example from the corresponding acid and base or by salt interchange.

Examples of the "pharmaceutically acceptable esters" are aliphatic esters, for example, lower alkyl ester e.g. methyl ester, ethyl ester, propyl ester, isopropyl ester, butyl ester, isobutyl ester, t-butyl ester, pentyl ester, 1-cyclopropylethyl ester, etc., lower alkenyl ester e.g. vinyl ester, allyl ester, etc., lower alkynyl ester e.g. ethynyl ester, propynyl ester, etc., hydroxy(lower) alkyl ester e.g. hydroxyethyl ester, lower alkoxy(lower)alkyl ester e.g. methoxymethyl ester, 1-methoxyethyl ester, etc., and aromatic esters, for example, optionally substituted aryl ester e.g. phenyl ester, tosyl ester, t-butylphenyl ester, salicyl ester, 3,4-di-methoxyphenyl ester, benzamidophenyl ester etc., aryl(lower)alkyl ester e.g. benzyl ester, trityl ester, benzhydryl ester, etc. Examples of the amides are mono- or di- lower alkyl amides e.g. methylamide, ethylamide, dimethylamide, etc., arylamide e.g. anilide, toluidide, and lower alkyl- or aryl-sulfonylamide e.g. methylsulfonylamide, ethylsulfonylamide, tolylsulfonylamide etc.

The term "pharmaceutically" is intended to be "ophthalmically" when used in connection with an ophthalmic composition.

Preferred examples of A include —COOH, —COOCH$_3$, —COOCH$_2$CH$_3$ and —COOCH(CH$_3$)$_2$.

The configuration of the ring and the α- and/or omega chain in the above formula (I) may be the same as or different from that in the primary PGs. However, the present invention also includes a mixture of a compound having a primary configuration and that of an unprimary configuration.

Examples of the typical compounds of the present invention are 15-keto-20-loweralkyl-PGAs to Fs and their derivatives e.g. $\Delta^2$-derivatives, 3R,S-methyl-derivatives, 6-oxo-derivatives, 5R,S-fluoro-derivatives, 5,5-difluoro-derivatives, 16R,S-methyl-derivatives, 16,16-dimethyl-derivatives, 16R,S-fluoro-derivatives, 16,16-difluoro-derivatives, 17S-methyl-derivatives, 17R,S-fluoro-derivatives, 17,17-difluoro-derivatives and 19-methyl-derivatives.

The component (a) may be in the keto-hemiacetal equilibrium by forming a hemiacetal between hydroxy group at position 11 and ketone at position 15.

The proportion of both tautomeric isomers, when present, varies depending on the structure of the rest of the molecule or kind of any substituent present and, sometimes, one isomer may predominantly be present in comparison with the other. However, in this invention, it is to be appreciated that the compounds used in the invention include both isomers. Further, while the compounds used in the invention may be represented by a structure or name based on keto-form regardless of the presence or absence of the isomers, it is to be noted that such structure or name does not intend elimination of the hemiacetal type of compounds.

In the present invention, any of the individual tautomeric isomers, a mixture thereof, or optical isomers, a mixture thereof, a racemic mixture, and other isomers such as steric isomers can be used in the same purpose.

Some of the compounds used in the present invention may be prepared by the method disclosed in Japanese Patent Publications (unexamined) No. A-108/1990 and No. A-96528/1990.

Alternatively, these compounds may be prepared by a process analogous to that described in the above publications in combination with the known synthetic method for the five-membered ring moiety.

In the process for preparing 13,14-dihydro-15-keto-compound:

A commercially available (–)-Corey lactone, which is used as a starting material, is subjected to Collins oxidation to give an aldehyde. The aldehyde is allowed to react with dimethyl (2-oxoalkyl)phosphonate anion to give an α,β-unsaturated ketone, and the resultant is reduced to ketone. The carbonyl group of the ketone is allowed to react with a diol to give a ketal, thereby protected, then a corresponding alcohol is obtained by elimination of the phenylbenzoyl group, and the resulting hydroxy group is protected with dihydropyran to give a tetrapyranyl ether. Thus, precursors of PGs wherein the ω-chain is 13,14-dihydro- 15-keto-alkyl can be obtained.

Using the above tetrapyranyl ether as a starting material, 6-keto-PG$_1$s with the group:

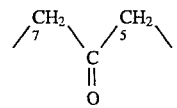

may be obtained as follows:

The tetrapyranyl ether is reduced using diisobutyl aluminium hydride and the like to give a lactol, which is allowed to react with a ylide obtained from (4-carboxybutyl)triphenylphosphonium bromide, and the resultant is subjected to esterification followed by cyclization, combining the 5,6-double bond and the C-9 hydroxyl group with NBS or iodine, providing a halide. The resultant is subjected to dehydrohalogenation with DBU and the like to give a 6-keto compound, which is subjected to Jones oxidation followed by deprotection to give the objective compound.

Further, $PG_2$s with the group:

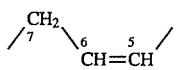

may be obtained as follows:

The above tetrapyranyl ether is reduced to the lactol, which is allowed to react with a ylide obtained from (4-carboxybutyl)triphenylphosphonium bromide to give a carboxylic acid. The resultant is subjected to esterification followed by Jones oxidation and deprotection to give the objective compound.

In order to obtain $PG_1$s with the group:

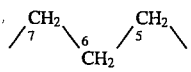

using the above tetrapyranyl ether as a starting material, in the same manner as $PG_2$ with the group:

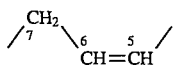

the 5,6-double bond of the resulting compound is subjected to catalytic reduction followed by deprotection. To prepare 5,6-dehydro-$PG_2$s containing a hydrocarbon chain of the formula:

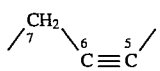

a monoalkyl copper complex or a dialkyl copper complex of the formula:

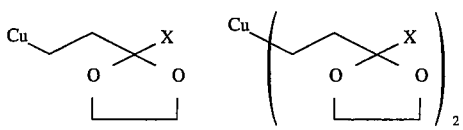

is subjected to 1,4-addition with 4R-t-butyldimethylsilyloxy- 2-cyclopenten-1-one, and the resulting copper enolate is seized with 6-carboalkoxy-1iodo-2-hexyne or a derivative thereof.

PGs containing a methyl group instead of a hydroxy group at the C-11 position may be obtained as follows: PGA obtained by Jones oxidation of the hydroxy group at the C-9 position of the 11-tosylate is allowed to react with a dimethyl copper complex to give 11-dehydroxy-11-methyl-PGE. Alternatively, an alcohol obtained after elimination of p-phenylbenzoyl group is converted to a tosylate. An unsaturated lactone obtained by DBU treatment of the tosylate is converted to a lactol. After introduction of an c-chain using Wittig reaction, the resulting alcohol (C-9 position) is oxidized to give PGA. PGA is allowed to react with dimethyl copper complex to give 11-dehydroxy-11-methyl-PGE. The resultant is reduced using sodium borohydride and the like to give 11-dehydroxy-11-methyl-PGF.

PGs containing a hydroxymethyl group instead of a hydroxyl group at the C-11 position is obtained as follow: 11-dehydroxy-11-hydroxymethyl-PGE is obtained by a benzophenone-sensitized photoaddition of methanol to PGA. The resultant is, for example, reduced using sodium borohydride to give 11-dehydroxy-11-hydroxymethyl-PGF.

16-Fluoro-PGs may be obtained using dimethyl (3-fluoro-2-oxoalkyl)phosphonate anion in the preparation of an α, β-unsaturated ketone. Similarly, 19-methyl-PGs may be obtained using a dimethyl (6-methyl-2-oxoalkyl)phosphonate anion.

The preparations in the present invention are not construed to be limited to them, and suitable means for protection, oxidation, reduction and the like may be employed.

The carbonate dehydratase inhibitor used as the component (b) in the present invention refer to agents capable of inhibiting enzymes which catalyze the reaction forming carbon dioxide and water from carbonate ($HCO_3^-$). Typical examples of such agents are compounds having one or more sulfamoyl groups combined to benzene or N- and/or S-containing 5- or 6- membered heterocyclic ring which is optionaly substituted by lower alkyl, halo, lower alkanoylamide or imido, and analogues thereof. Typically these have urine secretion improving effect and are exemplified by acetazolamide, methazolamide, diclofenamide, etc.

Since the component (a) has an activity of lowering ocular pressure without accompanying transient ocular hypertension as shogun by the primary PGs, the combination of (a) and (b) can be used for the treatment of various disease and conditions in which lowering of ocular pressure is desirous, for example glaucoma, ocular hypertension and other disease which accompanies increase in ocular pressure.

As used herein, the term "treatment" or "treating" refers to any means of control of a disease in a mammal, including preventing the disease, curing the disease, relieving the disease and arresting or relieving the development of the disease.

The combination has an advantage, by containing the component (b) in addition to the component (a), that it has a synergistically increased ocular hypotensive action, thus enabling reduce in dosage, and/or lowering the side-effect.

The ratio (a):(b) in the combination varies, without limitation, ordinarily within the range 1:0.5 to 1:200, preferably 1:1 to 1:100 and most preferably 1:2 to 1:50.

While the dosage of the component (a) varies depending on condition of the component(a) varies depending on condition of the patient, severity of the disease, purpose of the treatment, judgement of the physician and total dosage of the combination, it is ordinarily within the range 0.005 to 2% and preferably 0.01 to 1% by weight.

The dosage of the component (b) varies, for example, depending on the concentration of the component (a) and ordinarily within the range 0.005 to 20% and preferably 0.01 to 10% by weight.

The combination according to the present invention can be administered in the form of a pharmaceutical composition containing the components (a) and (b) and optionally other ingredients conveniently used in the ophthalmic, injective or oral composition, such as carrier, diluent or excipient.

The composition used according to the invention includes liquids such as solution, emulsion, dispersion etc. and semi-solids such as ophthalmic gel, ointment etc. Diluents for the aqueous solution or suspension include, for example, distilled water and physiological saline. Diluents for the non-aqueous solution and suspension include, for example, vegetable oils e.g. olive oil, liquid paraffin, mineral oil, and propylene glycol and p-octyldodecanol. The composition may also contain isotonization agents such as sodium chloride, boric acid, sodium citrate, etc. to make isotonic with the lacrimal fluid and buffering agents such as borate buffer, phosphate buffer, etc. to maintain pH about 5.0 to 8.0.

Further, stabilizers such as sodium sulfite, propylene glycol, etc., chelating agents such as sodium edetate, etc., thickeners such as glycerol, carboxymethylcellulose, carboxyvinyl polymer, etc. and preservatives such as methyl paraben, propyl paraben, etc. may also be added. these can be sterilized e.g. by passing through a bacterial filter or by heating.

The ophthalmic ointment may contain vaseline, Plastibase, Macrogol, etc. as a base and surfactant for increasing hydrophilicity. It may also contain geling agents such as carboxymethylcellulose, methylcellulose, carboxyvinyl polymer, etc.

In addition, the composition may contain antibiotics such as chloramphenicol, penicilin, etc. in order to prevent or treat bacterial infection.

A more complete understanding of the present invention can be obtained by reference to the following Preparation Examples, Formulation Examples and Test Examples which are provided herein for purpose of illustration only and are not intended to limit the scope of the invention.

PREPARATIONS

Preparations of 13,14-dihydro-15-keto-20-ethyl-$PGA_2$ isopropyl ester, 13,14-dihydro-15-keto-20-ethyl-$PGE_2$ isopropyl ester and 13,14-dihydro-15-keto-20-ethyl-$PGF_{2\alpha}$ isopropyl ester (cf Preparation chart I):

1) Preparation of 1S-2-oxa-3-oxo-6R-(3-oxo-1-trans-decenyl)- 7R-(4-phenylbenzoyloxy)-cis-bicyclo[3.3.0]-octane (3):

Commercially available (−)-Corey lactone (1) (7 g) was subjected to Collins oxidation in dichloromethane to give aldehyde (2). The resultant was allowed to react with dimethyl (2-oxononyl)phosphonate (4.97 g) anion to give 1S- 2-oxa-3-oxo-6R-(3,3-ethylendioxy-1-trans-decenyl)-7R-(4-phenylbenzoyloxy)-cis-bicyclo[3.3.0]-octane (3).

2) Preparation cf 1S-2-oxa-3-oxo-6R-(3-oxodecyl)- 7R-(4-phenylbenzoyloxy)-cis-bicyclo[3.3.0]-octane (4):

Unsaturated ketone (3) (7.80 g) was reduced in ethyl acetate (170 ml) using 5% Pd/C under hydrogen atmosphere. The product obtained after the usual work-up (4) was used in the following reaction.

3) Preparation of 1S-2-oxa-3-oxo-6R-(3,3-ethylenedioxy-decyl)- 7R-(4-phenylbenzoyloxy)-cis-bicyclo[3.3.0]-octane (5):

Saturated ketone (4) was converted to ketal (5) in dry benzene (150 mL) using ethylene glycol and p-toluenesulfonic acid (catalytic amount).

4) Preparation of 1S-2-oxa-3-oxo-6R-(3,3-ethylenedioxy-decyl)- 7R-hydroxy-cis-bicyclo[3.3.0]-octane (6):

To a solution of ketal (5) in absolute methanol (150 ml) was added potassium carbonate (2.73 g). The mixture was stirred overnight at room temperature. After neutralization with acetic acid, the resultant was concentrated under reduced pressure. The resulting crude product was extracted with ethyl acetate. The organic layer was washed with a dilute aqueous solution of sodium bicarbonate and a saline, and dried. The crude product obtained after evaporation was chromatographed to give alcohol (6). Yield; 3.31 g 5) Preparation of lactol (7):

Alcohol (6) (0.80 g) was reduced in dry toluene (8 ml) using DIBAL-H at −78 ° C. to give lactol (7).

6) Preparation of 13,14-dihydro-15,15-ethylenedioxy-20-ethyl-$PGF_2\alpha$ (8):

A DMSO solution of lactol (7) was added to ylide prepared from (4-carboxybutyl)triphenylphosphonium bromide (3.65 g). The reaction mixture was stirred overnight to give carboxylic acid (8).

7) Preparation of 13,14-dihydro-15,15-ethylenedioxy-20-ethyl-$PCF_2\alpha$ isopropyl ester (9):

Carboxylic acid (8) was converted to 13,14-dihydro-15,15-ethylenedioxy-20-ethyl-$PGF_2\alpha$ isopropyl ester (9) using DBU and isopropyl iodide in acetonitrile.

Yield; 0.71 g

8) Preparation of 13,14-dihydro-15-keto-20-ethyl-$PGF_2\alpha$ isopropyl ester (10):

13,14-Dihydro-15,15-ethylenedioxy-20-ethyl-$PGF_{2\alpha}$ isopropyl ester (9) (0.71 g) was kept in acetic acid/THF/water (3/1/1) at 40 ° C. for 3 hours. The crude product obtained after concentration under reduced pressure was chromatographed to give 13,14-dihydro-15-keto-20-ethyl-$PGF_2\alpha$ isopropyl ester (10).

Yield; 0.554 g

9 ) Preparation of 13,14-dihydro-15-keto-20-ethyl-$PGA_2$ isopropyl ester (12):

A solution of 13,14-dihydro-15-keto-20-ethyl-$PGF_2\alpha$ isopropyl ester (10) (0.125 g ) and p-toluenesulfonyl chloride (0.112 g) in pyridine (5 ml) was maintained at 0° C. for 2 days. According to the usual work-up, tosylate (11) was obtained.

Tosylate (11) was subjected to Jones oxidation in acetone (8 ml) at −25 ° C. The crude product obtained after the usual work-up was chromatographed to give 13,14-dihydro-15-keto-20-ethyl-$PGA_2\alpha$ isopropyl ester (2).

Yield; 0.060 g

10) Preparation of 13,14-dihydro-15,15ethylenedioxy-20-ethyl-11-t-butyldimethylsiloxy-$PGF_2\alpha$ isopropyl ester (13).

13,14-Dihydro-15,15-ethylenedioxy-20-ethyl-$PGF_{2\alpha}$ isopropyl ester (9) (3.051 g) was dissolved in dry N,N-dimethylformamide (25 ml), t-butyldimethylsilyl chloride (1.088 g) and imidazole (0.49 g) was added thereto. The resultant was stirred at room temperature overnight. The reaction mixture was concentrated under reduced pressure, and the resulting crude product was chromatographed to give 13,14-dihydro-15,15-ethylenedioxy-20-ethyl-11-t-butyldimethylsiloxy-$PGF_2\alpha$ isopropyl ester (13).

Yield; 2.641 g

11) Preparation of 13,14-dihydro-15,15-ethylenedioxy-20-ethyl-11-t-butyldimethylsiloxy-$PGE_2$ isopropyl ester (14):

13,14-Dihydro-15,15-ethylenedioxy-20-ethyl-11-t-butyldimethylsiloxy-$PGF_2\alpha$ isopropyl ester (13) (1.257 g) was subjected to Jones oxidation at −40 ° C. After the usual work-up, the resulting crude product was chromatographed to give 13,14-dihydro-15,15-ethylenedioxy-20-ethyl-11-t-butyldimethylsiloxy-$PGE_2$ isopropyl ester (14).

Yield; 1.082 g

12) Preparation of 13,14-dihydro-15-keto-20-ethyl-$PGE_2$ isopropyl ester (15):

To a solution of 13,14-dihydro-15,15-ethylenedioxy-20-ethyl-11-t-butyldimethylsiloxy-$PGE_2$ isopropyl ester (14) in acetonitrile was added hydrofluoric acid (46% aqueous solution). The mixture was stirred at room temperature for 40 minutes. The crude products obtained after usual work-up was chromatographed to give 13,14-dihydro-15-keto-20-ethyl-$PGE_2$ isopropyl ester (15).

Yield; 0.063 g (97%)

$^1$HNMR: δ0.86(3H,t,J=5 Hz), 2.20(6H,d,J=6.5 Hz), 1.05–2.96(29H,m), 4.01(1H,m), 4.95(1H,hept,J=6.5 Hz), 5.34(2H,m). MS (EI):m/z422 ($M^+$), 404 ($M^+$-$H_2O$), 345($M^+$-$H_2O$-i-$C_3H_2O$).

Preparation Chart
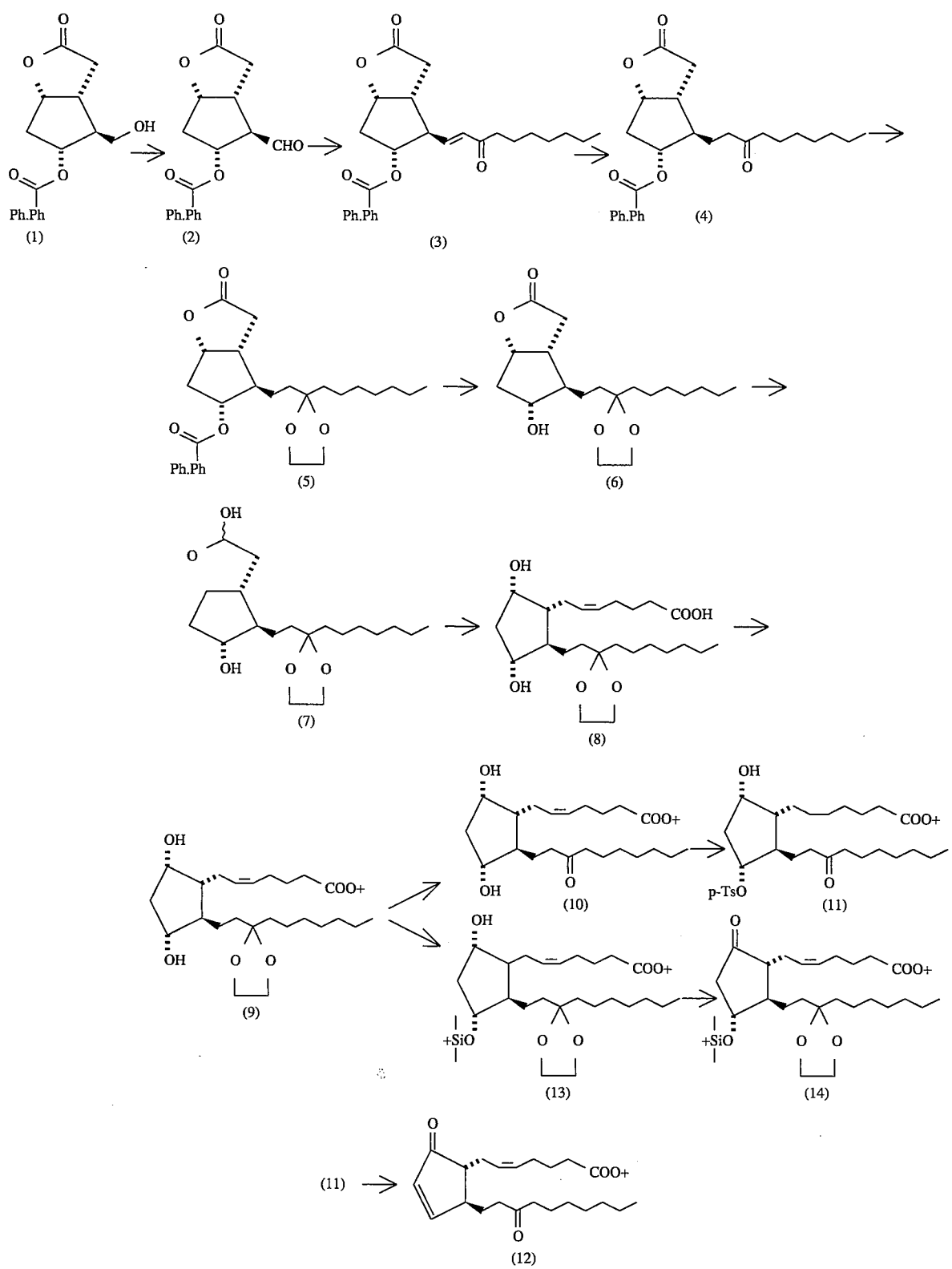

-continued
Preparation Chart

(14) →

(15)

+: iso-propyl

Formulation Example 1

(Ophthalmic solution)

| | |
|---|---|
| (A) Component (a) | 50 mg |
| Component (b) | 50 mg |
| (B) Physiological saline | 10 ml |

The above (A) and (B) were placed in separate vials. The vials were combined for preparing a solution on actual use.

Formulation Example 2

(Injectable solution)

| | (parts by weight) |
|---|---|
| Component (a) | 0.1 |
| Component (b) | 0.1 |
| Nonion surfactant | 2 |
| Distilled water for injection | 98 |

The above ingredients were mixed and sterilized to give an injectable solution.

Formulation Example 3

(Capsule)

| | (parts by weight) |
|---|---|
| Component (a) | 0.5 |
| Component (b) | 0.5 |
| Panasate* | 99 |

*Trade Mark

The above ingredients were mixed and filled in soft gelatine capsules.

Test Example 1

Japanese white rabbits (weight: 2.0–3.0 kg, 6 animals/group) were fixed and eyes were anesthetized by dropping 0.4% oxybuprocaine hydrochloride to eyes. The ocular pressure measured at 0.5–1 hour after the fixation was taken as the 0 hour value and values of pressure thereafter were measured in the course of time administering through the auricular vein a solution containing 0.2 mg/kg of each of the compounds shown in Test Plot and dissolved in distilled water for injection. An electronin pneumatonometer (Alcon) was used for measurement. Decrease in ocular pressure (mean value) at 3 hours after administration of each of the compounds was compared in the Table 1.

TABLE 1

| Test Plot | Compound | Dose (mg/kg: | Decrease in ocular pressure (mmHg) |
|---|---|---|---|
| 1 | 1 | 1.0 | −0.2 |
| 2 | 2 | 1.0 | −0.3 |

TABLE 1-continued

| Test Plot | Compound | Dose (mg/kg: | Decrease in ocular pressure (mmHg) |
|---|---|---|---|
| 3 | 1 | 1.0 | −2.9 |
| | 2 | 1.0 | |

Compound 1: Isopropyl (Z)-7-[(1R,2R,3R,5S)-3,5-dihydroxy-2-(3-oxodecyl)-cyclopentyl]-hept-5-enoate [13,14-dihydro-15-keto-20-ethyl-PGF$_2\alpha$ isopropyl exter,
Compound 2: Acedazolamide (Acetazolamide Sodium)

The above results show that the combined use of acetazolamide and Compound A results in a synergistic effect.

What we claim is:

1. A method for treatment of ocular hypertension which comprises ocularly administering, to a subject in need of such treatment, an oculo-hypotensively synergistic combination of (a) a 13,14-dihydro-15-keto-20-lower alkyl prostaglandin F or a pharmaceutically acceptable salt thereof or a lower alkyl ester thereof and (b) acetazolamide, or a pharmaceutically acceptable salt thereof, in an amount effective in treatment of ocular hypertension.

2. The method according to claim 1, in which the components (a) and (b) are administered in the ratio (a):(b) of 1:1 to 1:100.

3. The method according to claim 2, in which the components (a) and (b) are administered in the ratio (a):(b) of 1:1.

4. A method for treatment of ocular hypertension which comprises ocularly administering, to a subject in need of such treatment, an oculo-hypotensively synergistic combination of (a) a 13,14-dihydro-15-keto-20-ethyl prostaglandin F or a pharmaceutically acceptable salt thereof or a lower alkyl ester thereof and (b) acetazolamide, or a pharmaceutically acceptable salt thereof, in an amount effective in treatment of ocular hypertension.

5. The method according to claim 4, in which the components (a) and (b) are administered in the ratio (a):(b) of 1:1 to 1:100.

6. The method according to claim 5, in which the components (a) and (b) are administered in the ratio (a):(b) of 1:1.

7. A method for treatment of ocular hypertension which comprises ocularly administering, to a subject in need of such treatment, an oculo-hypotensively synergistic combination of (a) a 13,14-dihydro-15-keto-20-ethyl prostaglandin F$_{2\alpha}$ or a pharmaceutically acceptable salt thereof or a lower alkyl ester thereof and (b) acetazolamide, or a pharmaceutically acceptable salt thereof, in an amount effective in treatment of ocular hypertension.

8. The method according to claim 7, in which the components (a) and (b) are administered in the ratio (a):(b) of 1:1 to 1:100.

9. The method according to claim 8, in which the components (a) and (b) are administered in the ratio (a):(b) of 1:1.

* * * * *